US009370316B2

(12) United States Patent
Ewing et al.

(10) Patent No.: US 9,370,316 B2
(45) Date of Patent: Jun. 21, 2016

(54) MRI ESTIMATION OF CONTRAST AGENT CONCENTRATION USING A NEURAL NETWORK APPROACH

(75) Inventors: James R. Ewing, Royal Oak, MI (US); Hassan Bagher-Ebadian, Dearborn, MI (US)

(73) Assignee: HENRY FORD HEALTH SYSTEM, Detroit, MI (US)

( * ) Notice: Subject to any disclaimer, the term of this patent is extended or adjusted under 35 U.S.C. 154(b) by 470 days.

(21) Appl. No.: 12/600,750

(22) PCT Filed: May 19, 2008

(86) PCT No.: PCT/US2008/064165
§ 371 (c)(1),
(2), (4) Date: Apr. 5, 2010

(87) PCT Pub. No.: WO2009/020687
PCT Pub. Date: Feb. 12, 2009

(65) Prior Publication Data
US 2010/0198054 A1   Aug. 5, 2010

Related U.S. Application Data

(60) Provisional application No. 60/938,849, filed on May 18, 2007.

(51) Int. Cl.
*A61B 5/055* (2006.01)
*A61B 5/00* (2006.01)

(52) U.S. Cl.
CPC ............... *A61B 5/055* (2013.01); *A61B 5/7267* (2013.01)

(58) Field of Classification Search
CPC .............................. A61B 5/055; A61B 5/7267
See application file for complete search history.

(56) References Cited

U.S. PATENT DOCUMENTS

| 5,887,588 | A | * | 3/1999 | Usenius et al. ............... 600/410 |
| 7,738,683 | B2 | * | 6/2010 | Cahill et al. .................. 382/128 |
| 2005/0059881 | A1 | | 3/2005 | Balaban et al. |
| 2005/0065430 | A1 | | 3/2005 | Wiethoff et al. |

OTHER PUBLICATIONS

Ewing et al, Platlak Plots of Gd-DTPA MRI Data Yield Blood-Brain Transfer Constants Concordant with those of 14C-Sucrose in Areas of Blood-Brain Opening, Magnetic Resonance in Medicine 50:283-292 (2003).*
International Search Report dated Jan. 15, 2009 in PCT/US 08/64165. (1 page).

* cited by examiner

*Primary Examiner* — Ruth S Smith
(74) *Attorney, Agent, or Firm* — Honigman Miller Schwartz and Cohn LLP; Fernando Alberdi; Jonathan P. O'Brien

(57) ABSTRACT

The invention comprises systems, methods, and apparatus to correlate changes in MRI data with CA concentration, using an adaptive neural network In MRI techniques, CAs are used to estimate vascular properties such as blood flow, blood volume, and transfer constant of tissue microvessels However, the relationship between the contrast in the MRI image and the contrast agent concentration is not linear, instead depending on factors such as the nature of the sequence, the nature of the tissue, and the tissue concentration of contrast agent, and thus limiting the reliability of vascular properties using MRI.

6 Claims, 6 Drawing Sheets

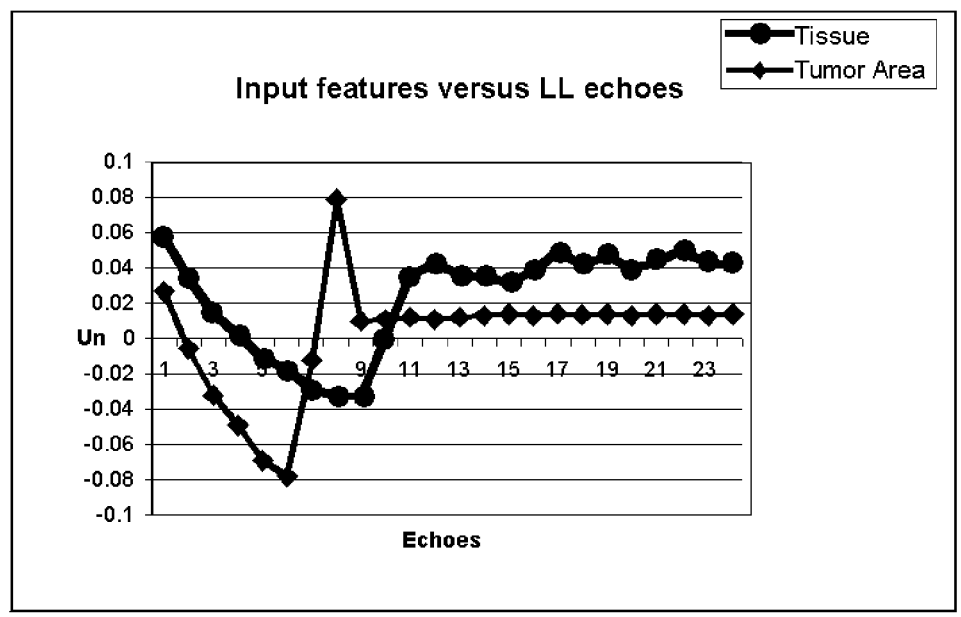
FIG. 3: {$U_n$} versus TOMROP echo number (1-24) from two ROI's sampled in normal tissue and tumor.

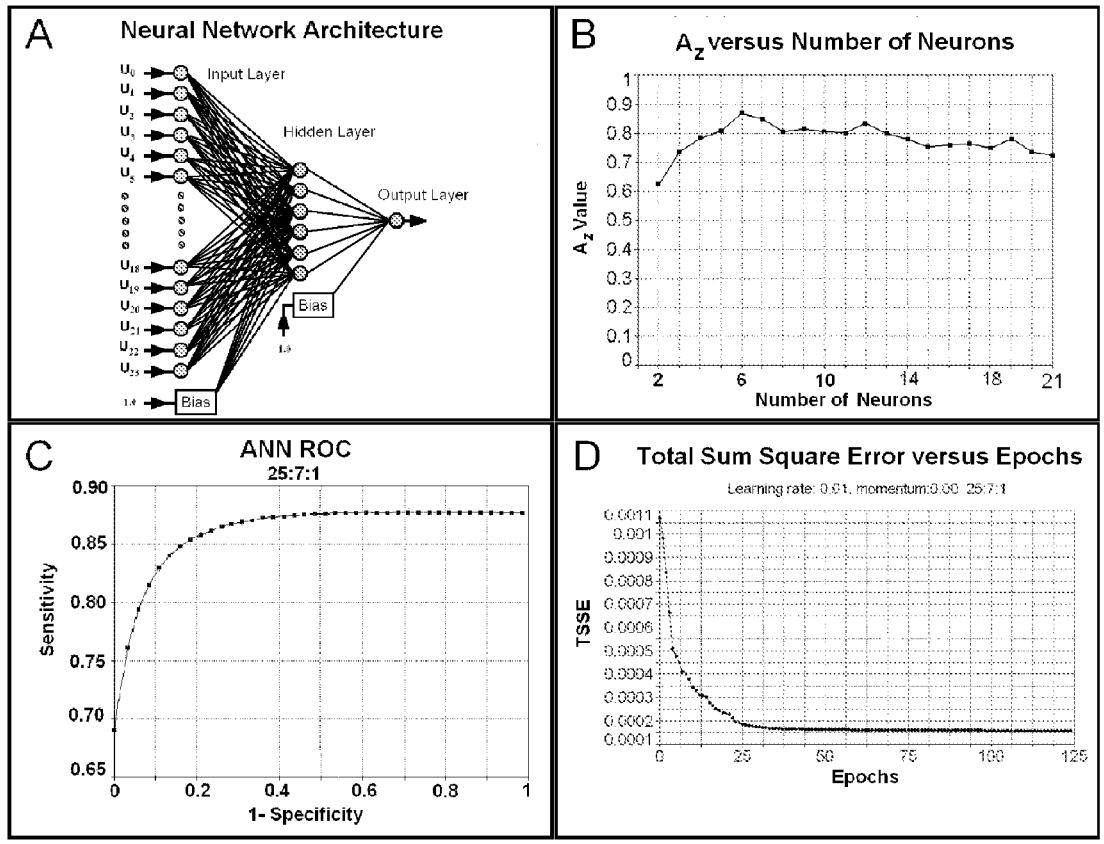

FIG. 4A: Feed-forward MLP Neural Network with one hidden layer, 24 input neurons, 6 neurons in the hidden layer and one output neuron for CA concentration.

FIG. 4B: $A_z$ Test versus number of neurons (Max ($A_z$)=0.86 for 6 neurons + 1 bias).

FIG. 4C: ANN-ROC curve generated by 400 epochs during KFCV procedure for optimal ANN with 25:7:1 architecture. The AUROCC for this curve is 0.86.

FIG. 4D: Total Sum Square Error versus epochs for the optimal ANN (25:7:1) using 8100 samples and learning rate of 0.001. Note the stopping error is 0.000158 for all divided K-Fold sets.

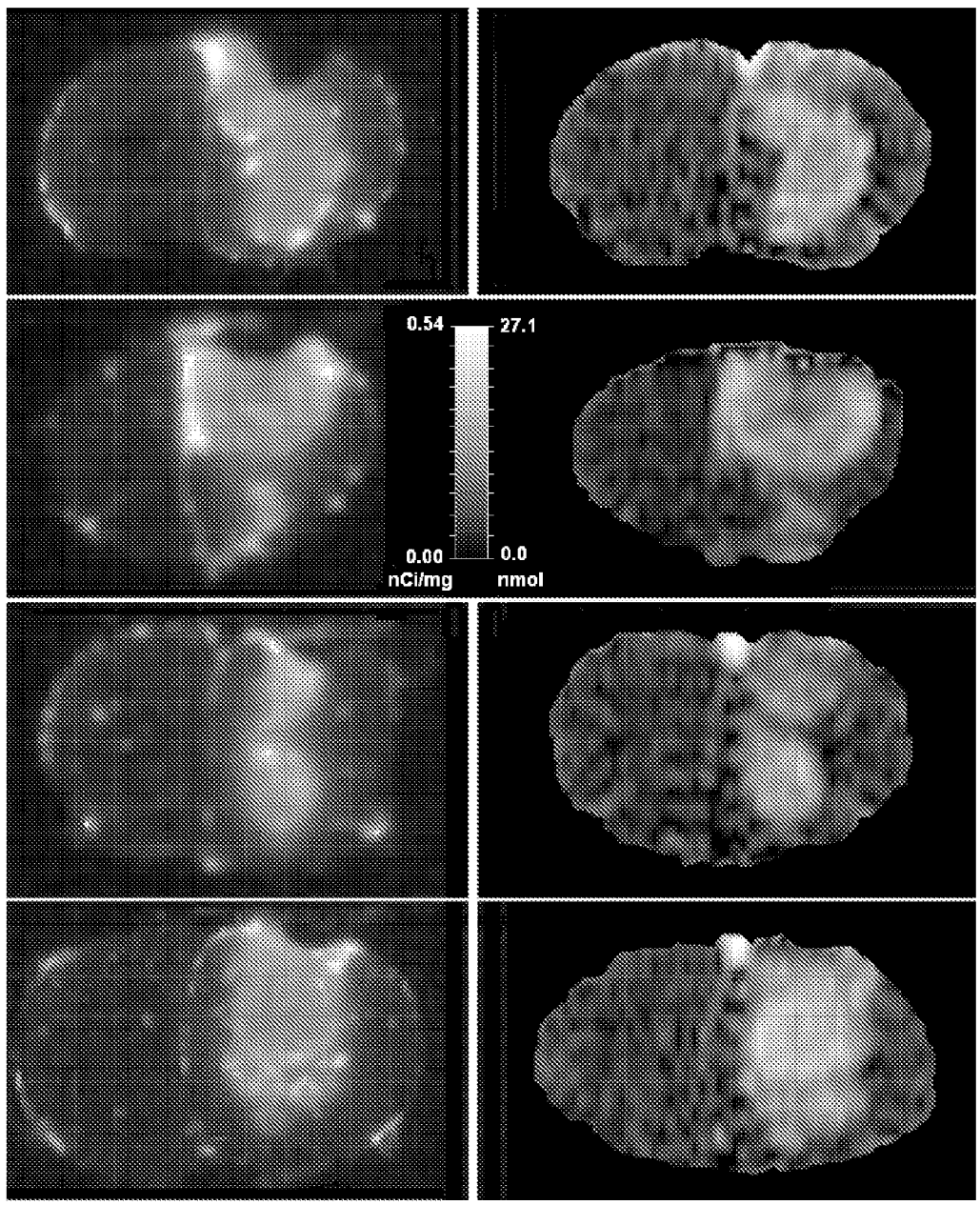
FIG. 5: Left column: Gold standard maps of RISA concentration (nCi/mg). Right column: Gd concentration (nmol) calculated from ANN responses after standardization and masking for brain areas.

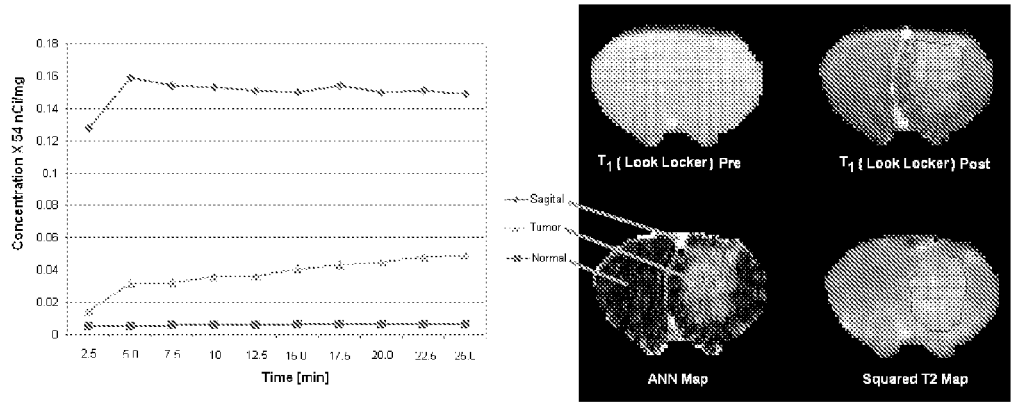

FIG. 6: An ANN predictor of contrast agent concentration, using as inputs the set $[\{Un\}, T_2^2]$. The sagittal sinus, tumor ROI, and normal tissue concentrations are plotted as a function of time across the duration of the experiment. The ratio of blood to normal tissue concentration is about 27:1, which is very close to the expected ratio for plasma concentrations in large vessels *versus* microvessels.

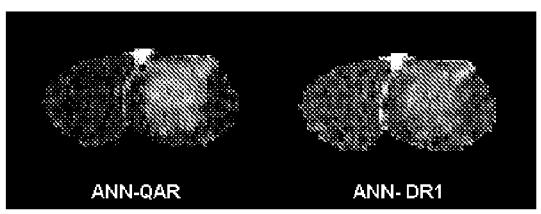

FIG. 7: Left: The output of an ANN trained using the input feature vectors of Eq 9, plus $T_2^2$, with ARGs as the training set. Right: the output of an ANN trained with the input feature vectors of Eq 9, plus $T_2^2$, but using $\Delta R_1$ as the training set.

MRI ESTIMATION OF CONTRAST AGENT CONCENTRATION USING A NEURAL NETWORK APPROACH

PRIORITY CLAIM

This application is a National Phase application claiming the benefit of International Application No. PCT/US2008/064165, filed May 19, 2008, which claims priority from U.S. Provisional Patent Application No. 60/938,849, filed May 18, 2007, the complete disclosures of which are each hereby incorporated in full.

STATEMENT REGARDING FEDERALLY SPONSORED RESEARCH OR DEVELOPMENT

Certain work underlying the invention was funded in part by the NIH grants RO1 HL70023 MRI Measures of Blood Brain Barrier Permeability and NINCDS PO1 NS23393 Center for Stroke Research. The government may have certain rights in the invention.

FIELD OF THE INVENTION

Embodiments of the invention relate to the field of magnetic resonance imaging.

BACKGROUND

Magnetic resonance imaging ("MRI") is a non-invasive method used to render images of the inside of an object. In medical applications, it is often used to demonstrate pathological or other physiological conditions or alterations of living tissues. As some examples only, in MRI techniques, contrast agents ("CA" or "CAs") are used to estimate vascular properties such as blood flow, blood volume, and transfer constant of tissue microvessels, the latter being an index of the vascular permeability. However, the relationship between the contrast in the MRI image and the CA concentration is often not linear. Instead, it can depend on the nature of the sequence, the nature of the tissue, and the tissue concentration of contrast agent, limiting the reliability of estimates of vascular properties using MRI CAs.

Thus, although CAs are widely used in MRI studies, their ability to quantify such physiological variables as blood flow (Ostergaard et al. 1996a; Ostergaard et al. 1996b; Rempp et al. 1994), vascular volume (Boxerman et al. 2006; Rempp et al. 1994), and vascular transfer constant (Ewing et al. 2006; Tofts et al. 1999) can be limited by the mixed (e.g., $T_2$* and $T_1$), and/or nonlinear (Landis et al. 2000; Li X. et al. 2005; Yankeelov et al. 2003), contrast mechanisms encountered.

Currently, physiological measurements in humans most often employ chelated gadolinium in the form of Gd-DTPA or similar low-molecular weight CA. In animals, Gd-DTPA-albumin complex (Nagaraja et al. 2006) can be used in concentration-time studies to quantify tumor vascular transfer constant ($K_1$ or $K^{trans}$) and extravascular, extracellular leakage volume ($v_e$). In humans, the concentration of CA is most commonly inferred from changes in $T_2$* (Johnson et al. 2004; Ostergaard et al. 1996a; Ostergaard et al. 1996b; Rempp et al. 1994), although for purposes of measuring $K_1$, the chosen mechanism may be that of $T_1$ contrast (Daldrup-Link et al. 2004). However, as noted, changes in $R_2$ ($R_2=1/T_2$) and $R_2$* ($R_2^*=1/T_2^*$) and $R_1$ (Landis et al. 2000; Li, X. et al. 2005; Yankeelov et al. 2003) ($R_1=1/T_1$) are not generally linear in CA concentration, particularly when CA occupies both vascular and extravascular tissue compartments. Since in MRI physiological studies, the measurement of CA concentration plays a crucial role in quantification and estimation of kinetic model parameters, these nonlinearities, if ignored, may lead to systematic errors that substantially undermine the reliability of the measurement.

BRIEF DESCRIPTION OF THE DRAWINGS

The present invention will now be described, by way of example only and without disclaimer of other embodiments, with reference to the accompanying drawings, in which:

FIG. 3 is an example of the sequence of features, $\{U_n\}$ versus TOMROP echo number (1-24) from two ROI's sampled in normal tissue and tumor;

FIG. 4A shows a Feed-forward MLP Neural Network with one hidden layer, 24 input neurons, 6 neurons in the hidden layer and one output neuron for CA concentration;

FIG. 4B shows an $A_z$ Test versus number of neurons (Max $(A_z)$=0.86 for 6 neurons+1 bias);

FIG. 4C is an ANN-ROC curve generated by 400 epochs during KFCV procedure for optimal ANN with 25:7:1 architecture. The AUROCC for this curve is 0.86;

FIG. 4D is a Total Sum Square Error versus epochs for the optimal ANN (25:7:1) using 8100 samples and learning rate of 0.001. Note the stopping error is 0.000158 for all divided K-Fold sets;

FIG. 5 shows comparative concentrations of contrast agent: Left column: Gold standard maps of RISA concentration (nCi/mg). Right column: Gd concentration (nmol) calculated from ANN responses after standardization and masking for brain areas;

FIG. 6 shows an ANN predictor of contrast agent concentration, using as inputs the set $[\{Un\}, T_2^2]$; and FIG. 7 shows, at the left, the output of an ANN trained using the input feature vectors of Eq 9, plus $T_2^2$, with ARGs as the training set, and at the right, the output of an ANN trained with the input feature vectors of Eq 9, plus $T_2^2$, but using $\Delta R_1$ as the training set.

Figure 1:
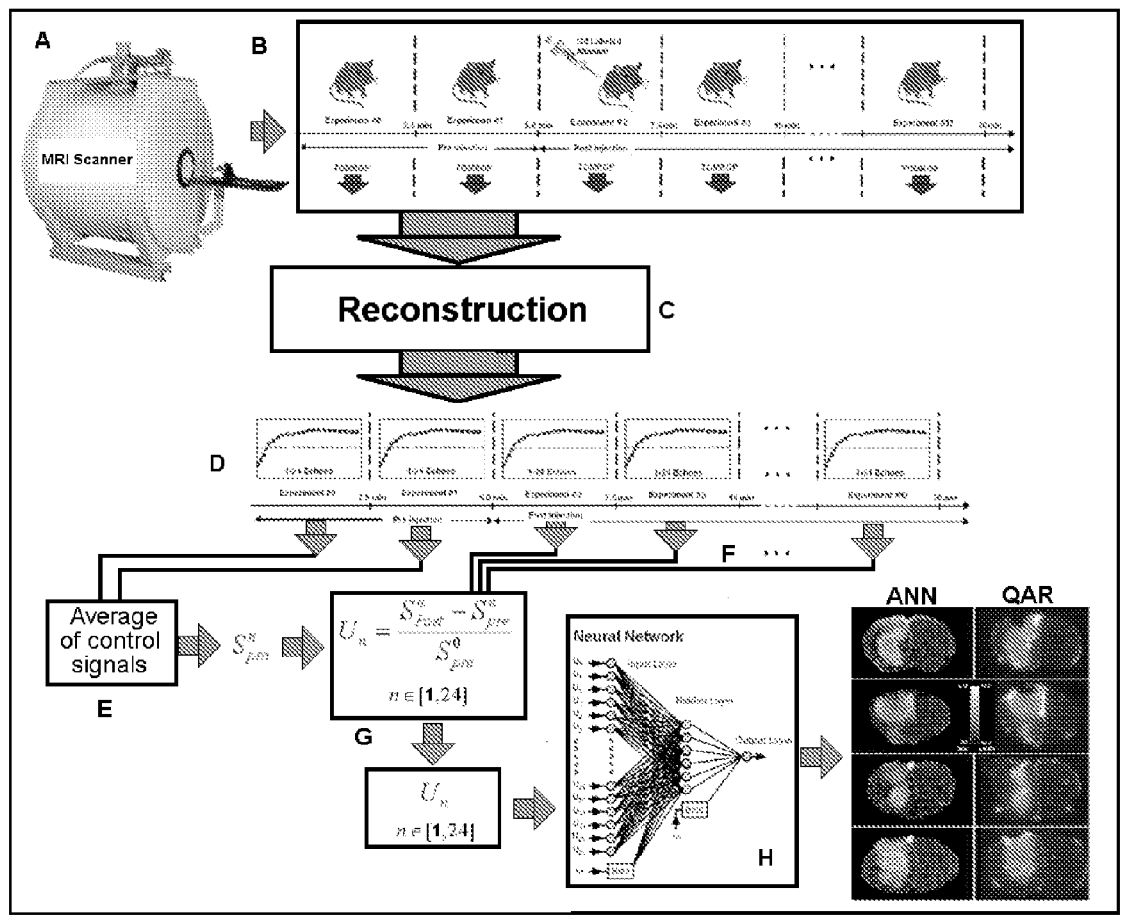
FIG. 1 shows a diagram of certain processes associated with the creation and use of an Adaptive Neural Network predictor for contrast agent tissue concentration in accordance with some embodiments.

Other aspects of embodiments will be apparent to those skilled in the art after reviewing the drawings and the detailed description below.

DETAILED DESCRIPTION

In some embodiments, without limitation and without disclaimer of any embodiments not expressly described herein, the invention comprises systems, methods, and apparatus to correlate changes in MRI data with CA concentration, using an adaptive neural network. In MRI techniques, CAs are used to estimate vascular properties such as blood flow, blood volume, and transfer constant of tissue microvessels. However, the relationship between the contrast in the MRI image and the contrast agent concentration is not linear, instead depending on factors such as the nature of the sequence, the nature of the tissue, and the tissue concentration of contrast agent, and thus limiting the reliability of vascular properties using MRI.

To address this issue, we have developed novel systems, methods, and apparatus to relate MRI contrast and contrast agent concentration, using an adaptive neural network ("ANN"). An ANN is an interconnected group of artificial neurons that uses a mathematical or computational model for information processing. Such networks are typically nonlinear statistical data modeling tools used to model complex relationships between inputs and outputs or to find patterns in data. In most cases, the ANN is "adaptive" in the sense that it changes its structure, or "learns," based on external or internal information that flows through the network. Thus, one can "train" an ANN to learn to recognize differences in test data sets based on inputted information.

ANNs are used in science and engineering for such widely varying tasks as decision making and point value estimation (McCulloch and Pitts 1943). One advantage of employing an ANN for nonlinear point estimation is its ability to be used as an arbitrary function approximation mechanism, which 'learns' from observed data (Duda et al. 2001); that is, the utility of ANN models is that they can be used to infer a function from observations (Gurney 1997). This property is particularly useful in applications where complexity makes the design of an accurate model impractical (Bagher-Ebadian et al. 2004; Duda et al. 2001; Freeman and Skapura 1991; Looney 1997); in many estimation problems, ANN's have been found to be fast, accurate, and noise adaptable (Haykin 1999). Application of ANN's in the field of dynamic contrast enhanced imaging has been limited to tissue segmentation and lesion classification (see Galbraith et al. 2003, and Wismüller et al. 2006, for examples of such applications).

In some embodiments, without limitation, input data is comprised of a series of MRI images before and after the injection of Gd-labeled serum albumin as a contrast agent. For comparison, an ANN training criterion is generated comprised of images of known concentrations of tissue radioactive serum albumin from a quantitative autoradiograph experiment. This serves as a "gold standard" for training the ANN to understand the relationship between MRI image changes and contrast agent concentration. In accordance with some embodiments, the ANN can successfully estimate the contrast agent concentration in tissue and is in good agreement with classic methods of evaluating same. Consequently, a trained ANN in accordance with some embodiments can provide a good and stable estimate of MRI contrast agent concentration in tissues from MRI signals in different time points after injection. One advantage conferred, among others, is that some embodiments provide a fast, nonlinear and reliable estimator to predict and estimate contrast agent concentration in tissue using MRI signals.

EXAMPLES

The following examples of some embodiments of the invention are provided without limiting the invention to only those embodiments described herein and without disclaiming any other embodiments.

Given a "gold-standard" map of CA concentration, an ANN is trainable to directly estimate CA concentration from MRI image sets in which the time-varying behavior of the images depends, albeit nonlinearly, on CA concentration. Some of our studies using TOMROP ("T One by Multiple Read Out Pulses") image sets as inputs in a set of tubular gel phantoms are supportive. In accordance with some embodiments, without limitation, an ANN for estimating CA concentration in the brain tissue of 9 male Fisher rats, using as inputs TOMROP signal changes after injection of Gd-BSA in a 9 L rat model of cerebral gliosarcoma (Ewing et al. 2006), was designed, trained, optimized, and tested. The MRI experiment was followed by quantitative autoradiography ("QAR") using radioiodinated serum albumin ("RISA"), thus essentially replicating the MRI as to its timing, procedures, and indicator. The autoradiogram of the QAR procedure served as the training set.

Some embodiments comprise a method for linearizing the relationship between MRI contrast and CA concentration using an ANN. As one example only, among others, MRI data was acquired at 7 Tesla in a rat model of cerebral tumor using a Look-Locker imaging sequence named TOMROP, which produces a sequence of images after an initial inversion of the MRI signal. ANN inputs were a sequence of raw images, and combinations of raw images, from one slice of the Look-Locker imaging sequence before and approximately 25 minutes after injection of Gd-labelled serum albumin. The ANN training criterion was an autoradiographic image of tissue radioactive serum albumin from a quantitative autoradiography experiment performed soon after the MRI experiment. Autoradiographic images were matched to the MRI image and summed to match the MRI slice thickness. The trained ANN produced a direct estimate of the contrast agent concentration at 25 minutes after the injection of Gd-albumin, and in the intervening time points at which TOMROP images were acquired. The ANN method of directly estimating contrast agent concentrations can be generalized to other MRI sequences, thus providing reliable estimates of blood volume, blood flow, and transfer constant.

In MRI, contrast agents are used to create differential contrast in regions of tissue (usually diseased tissue). These vessels are differentially more porous to the contrast agent than the surrounding vasculature. In the brain, since normal vessels are impermeable to all MRI contrast agents, this is an especially useful procedure. In terms of estimating vascular parameters, blood flow, blood volume, and transfer constant (vascular permeability), the theory and practice of point estimation of vascular parameters using the uptake and clearance of CAs is well established from prior practice using radionuclides. A major remaining problem, which is addressed by some embodiments of the invention, is that of a reliable estimate of CA concentration versus time using MRI imaging techniques. This problem arises because the relation rates, $R_1$ ($R_1=1/T_1$), $R_2$ ($R_2=1/T_2$), and $R_2^*$ ($R_2^*=1/T_2^*$), while linear in CA concentration in gels, are not linear in CA concentration in tissue, where the compartmentalization of water and/or CA becomes an important consideration.

Because $T_1$ is generally long with respect to mean diffusion times over cellular distances, in the absence of restriction it might be expected that most of the protons of water are equivalent, and therefore that $T_1$ decay is monoexponential. Thus, more robust techniques for estimating CA concentration via MRI contrast generally utilize measures of $T_1$ and/or $T_1$-weighted images. For instance, a recent study of angiogenesis and permeability in tumor vascular beds first determined $R_1$ maps by a progressive-saturation method, and then followed by a saturated uptake (TR=50 ms, tip-angle=90°) experiment, in which the change in contrast was used to infer the change in CA concentration. Single-point estimates of $R_1$ assume that the magnetization recovery remains monoexponential in tissue. This has been shown to not to be the case, and this means that a single-point estimate of $R_1$ is not linear in CA concentration. The degree to which an estimate of CA concentration based on the linear assumption deviates from the true concentration depends on CA concentration, distribution space, the original relaxation rates in the compartments of distribution, and tip-angle and repetition time of the MRI sequence.

Because even the fastest $T_1$-based MRI sequences are comparatively slow, most current procedures use MRI techniques based on $T_2$ and $T_2^*$ contrast, with echo-planar, spiral, or propellor readout, thus allowing more complete coverage of the organ (usually brain). Estimates of CA concentration based on $T_2^*$ are very widely employed, particularly in dynamic contrast enhancement ("DCE") estimates of cerebral blood volume and cerebral blood flow ("CBV" and "CBF"). In the case that the CA remains intravascular, the method is well accepted, although there is a substantial possibility for artifacts because of profound difficulties in assessing the shape and timing of the arterial input function.

In the event that substantial leakage of contrast agent from infra- to extra-vascular space takes place, using $T_2^*$ contrast techniques, a strong and competing $T_1$ contrast effect is often noticed in areas of pathology because of the necessity of short (about 1 s) repetition times needed to estimate CBF. As a first-order tactic to minimize the competing $T_1$ contrast, pre-loading with contrast agent has been proposed, with some success. However, this approach does not allow an estimate of transfer constant. An alternative, which lengthens the repetition time of the experiment, thus discarding the estimation of CBF and estimating only CBV and K1, the transfer constant, has also been proposed. Neither of these techniques is without substantial problems in estimating CBF tissue concentrations, and also in estimating the arterial input function ("AIF").

Some embodiments employ an ANN to estimate the concentration of a gadolinium-labeled MRI CA in tissue. We have designed, trained and optimized an ANN to directly estimate Gd-labeled albumin concentration in rat models of cerebral tumor and tissue. A set of TOMROP sequences before and after contrast agent injection were shown to the ANN as the input training set. A corresponding autoradiograph, acquired as part of a Quantitative Autoradiography ("QAR") experiment using Radioiodinated Serum Albumin ("RISA") as an indicator, was used as a "gold standard" for training the ANN to understand the contrast agent concentration.

As one example, only, using an MRI TOMROP image set, an ANN was trained to directly estimate the concentration of a contrast agent ("CA"), Gd-bovine serum albumin ("Gd-BSA"), in tissue. In 9 rats implanted with a 9 L cerebral tumor, MRI acquisition of TOMROP inversion-recovery data was followed by quantitative autoradiography ("QAR") using radioiodinated serum albumin ("RISA"). QAR autoradiograms were used as training set for the ANN. Pre-contrast and 25 minute post-contrast TOMROP image sets were shown to the ANN in the form of a physical feature set related to 24 inversion-recovery images; QAR autoradiograms at 30 minutes after injection of RISA were taken as the training standard for the network. After training and optimization the ANN produced a map of Gd-BSA concentration. The ANN's prediction of CA concentration at 25 minutes after injection was well correlated ($r=0.82$, $p<0.0001$) with the autoradiograms.

For all training set studies, QAR followed quickly after MRI. The pre- and 25 minute post-contrast TOMROP signals of 9 rats were shown to the ANN; their autoradiograms taken at 25 minutes after injection of RISA were considered as the gold standard for training. The ANN was trained, optimized and tested over the real data and QAR to produce a preliminary map of Gd-albumin concentration. A map of the difference between the pre-injection longitudinal relaxation rate, $R_1$, and $R_1$ at 20 minutes post-injection, i.e., delta R1 ($\Delta R_1$), was used to train the second ANN in order to standardize the map of Gd-BSA (Gadolinium-labeled Bovine Serum Albumin) concentration produced in the previous step. To evaluate the ability of the trained ANN to estimate Gd-BSA concentration versus time, the TOMROP signals of 9 intermediate time points (between 0 to 25 minutes) were inputted to the trained ANN and the temporal response of the ANN was checked against changes in the $R_1$. Results indicate that the ANN can estimate the contrast agent concentration in tissue and is in a good agreement with classic methods. Therefore, in accordance with some embodiments of the invention, the trained ANN's provide a good and stable estimate of MRI contrast agent concentration in tissue from MRI signals in different time points after injection.

In some embodiments, an ANN was designed, trained and tested for a problem in which the prediction of a quantity suffers from lack of accurate modeling. Thus some embodiments of the invention provide a fast, nonlinear and reliable estimator to predict and estimate CA concentration in mammalian or other suitable biological tissue or compartment using MRI signals. Some advantages conferred are that no other technique shows promise for accurately estimating contrast agent concentration from fast MRI sequences, and that the ANN procedure, once trained, can provide such an estimate nearly in real time as the MRI data is acquired and reconstructed into images. Since CAs play very important roles in diagnosis and therapeutic domains, embodiments can facilitate the extraction of accurate and useful functional information from perfusion and DCE studies in MRI.

Materials and Methods—

General: In FIG. 1, certain processes associated with the creation and use of the ANN in some embodiments, without limitation, are diagrammed. The subject (as some examples only, a mammal, including without limitation, a human patient, or other animal) is prepared by venous cannulation for the injection of contrast agent and placed in an MRI scanner (A). After location, coil tuning, and magnetic field shimming, a conventional multi-point $T_2$ image set is acquired, and then two pre-contrast Look-Locker (LL) data acquisitions are acquired, so that a pixel-by-pixel baseline map of the longitudinal relaxation rate, $R_1$ ($R_1=1/T_1$) can be formed (B). Following the two baseline LL acquisitions, another LL acquisition is started, and Gd-tagged albumin injected across a period of about 1 minute. In some embodiments, without limitation, 9 or more LL's are taken (B). Following the LL acquisitions, a $T_1$-weighted post-contrast image is acquired.

After the completion of MRI procedures, the MRI data is reconstructed (C), yielding for each LL set a pixel-by-pixel record of the recovery of tissue magnetization after its initial inversion (D). The two pre-contrast inversion-recovery records are averaged (E) to form the reference signal $S^0_{pre}$, and then the feature set $\{U_n\}$ is formed (G) as an input to the ANN (H). Another feature set (not shown in the diagram) presented to the ANN is the pixel-by-pixel value of $T_2^2$. The trained ANN then produces a pixel-by-pixel estimate of contrast agent concentration. Once trained, the ANN can be used at a particular field strength for both human and animal predictions of contrast agent concentration.

For training the ANN, animal models are useful, although data may also be acquired from other suitable sources. Following the MRI procedures, the animal is removed from the magnet for quantitative autoradiography ("QAR") using radioiodinated serum albumin ("RISA") as a tracer. This choice of tracer means that a nearly-identical indicator is used in both the MRI and QAR experiments, so that the autoradiograms subsequently produced can be used as training sets for the ANN (bottom right illustration of FIG. 1). These training sets are then shown to the ANN in its training mode, and the internal weights of the nodes are adjusted to optimize the predictive ability of the ANN.

Figure 2:
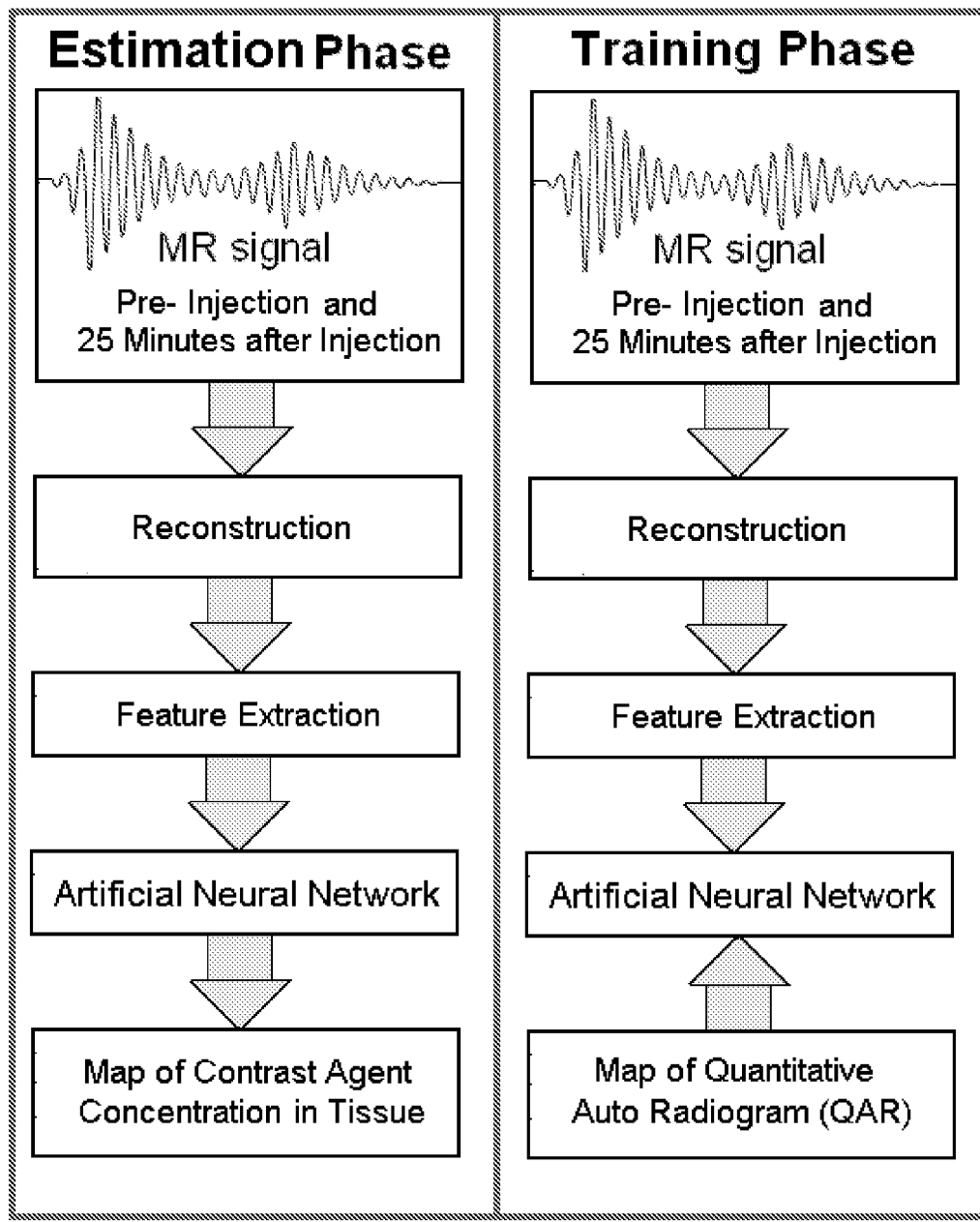
FIG. 2 shows a flow chart of certain steps in training (right-hand stack) and using (left-hand stack) an Adaptive Neural Network predictor for contrast agent tissue concentration in accordance with some embodiments.

FIG. 2 shows the flow of data through certain processing steps to train (right-hand stack) and use (left-hand stack) the ANN for predicting contrast agent tissue concentration in some embodiments, without limitation and without disclaimer of other embodiments. MRI data is acquired as a time-domain signal and reconstructed to form a pixel-by-pixel image of signal intensity following inversion of the magnetization in the tissue. Other MRI data is also summarized (e.g. $T_2$ maps) Features are extracted from the time-dependent recovery of magnetization after inversion, as well as the other MRI data (e.g. $T_2^2$ maps are formed). These features are input to the input neurons of an ANN.

In the training mode, the weights of the neuronal interconnections are adjusted to optimize the ability of the ANN to predict the image set, following procedures described previously.

Animal Studies: As part of our studies to compare MRI estimates of transfer constant to QAR estimates (results not included here), nine animals (Fisher 344 rats) with 9 L tumor (Ewing et al. 2006) were studied. Mean tumor age was 14.6±0.7 days (range 14 to 16 days) for all animals. In MRI procedures (see below), two initial TOMROP image sets (24 echoes per image set) were followed by the injection of a prepared Gd-DTPA-labeled albumin (Gd-BSA) solution (Nagaraja et al. 2006), and then ten more TOMROP data sets were collected (Ewing et al. 2006). Extravasation of Gd-BSA occurred within the tumors and at tumor borders in all animals. The last set of TOMROP images was used in training the ANN, since it corresponded most closely in time post-injection to the QAR data set subsequently taken using RISA as the indicator in the animal data.

Inputs and Training Sets for the ANN-MRI Studies:

TOMROP (Brix et al. 1990) image sets formed the data input to the ANNs, while the training sets were maps of RISA activity derived from autoradiograms. Established procedures (e.g., Ewing et al. 2006; Ewing et al. 2003) were used to acquire a set of 24 TOMROP inversion-recovery images at 50 ms intervals. Matrix size was 128×64, FOV 32 cm, flip angle approximately 18°, three 2 mm slices, total imaging time 145 Sec per TOMROP image set.

Quantitative Autoradiography ("QAR"): Radioiodinated ($^{125}$I) bovine serum albumin ("RISA") (Specific activity, 333 Ci/mmol; PerkinElmer Life Sciences, Inc. Boston, Mass., USA) and $^{125}$I microscales (Amersham Biosciences, Piscataway, N.J., USA) were obtained commercially and used as received. Immediately after MRI, the rats were removed from the plexiglass holder and kept anesthetized on a warm water-recirculated rubber mat. A femoral artery was cannulated using PE-50 tubing. About 100 μCi of RISA in 1 ml normal saline was injected through the tail vein as a slow bolus over a minute, as in the MRI injection of Gd-BSA. Timed arterial blood samples were obtained to establish the arterial input curve. Thirty minutes after the bolus injection, the rat was decapitated swiftly and the head was immediately frozen in 2-methylbutane cooled to −45° C. This procedure generally preserves intracerebral fluids such as blood and cerebrospinal fluid and maintains the normal contours of the brain (Blasberg 1983; Nakagawa 1987). The frozen brain was dissected in a chest freezer without allowing it to thaw and embedded in M-1 embedding matrix (Thermo-Shandon, Pittsburgh, Pa., USA).

The embedded brain was then cut into a series of five 20 μm thick sections at 200 μm intervals in a cryostat (Microm GmbH, Walldorf, Germany) set to −18° C. The sectioning began at the rostral end of the brain where the tumor cells were implanted and continued to the striate cortex. The first and the last sections from each 400 μm block were placed on serially numbered glass slides and Nissl stained to visualize tumor tissue. The middle three sections were picked up on serially numbered cover glasses and immediately dried on a hot plate set to 60° C. After drying, the cover glasses were glued in their serial order to cardboard sheets. These sheets and a set of $^{125}$I microscales containing known amounts of radioactivity were exposed to Kodak Biomax MR scientific imaging film (Eastman Kodak Co., Rochester, N.Y., USA). The microscale standards were of the same thickness (20 μm), and approximately the same density, as the tissue slides. Films were developed after 7-10 days of exposure to obtain the autoradiograms.

A flat bed scanner (Cannon-N676U) with an 8-bit grayscale resolution was employed to convert the film information to digital images at a resolution of 400 DPI, corresponding to 0.0635 mm/pixel. Thus, for each pixel in the TOMROP image, about 16 of the pixels from the scanner could be summed and then averaged, producing an estimate of film density with a resolution of about one part in 4000. Using the microscale standards (see below), this film density was then converted to an estimate of RISA concentration, in units of nCi/mg.

As noted, $^{125}$I microscale standards with known activities were used to calibrate the scanned images. Before using the standard bars to calibrate the film intensity, radio-interaction and Superposition effects for all standard activity bars were corrected by the Sievert Integral Function ("SIF") method (Williamson, 1996). After SIF correction, a polynomial function was fitted to the curve of standard bar activity versus image intensity. After intensity to activity conversion, the autoradiograph contact sheet was examined and a slice was chosen that best matched the selected MRI slice, then registered to the MRI slice and used as a gold-standard image.

All image analysis and registration tasks were performed on a SUN UltraSparc2 workstation (Sun Microsystems Inc., Mountain View, Calif.) using the Eigentool image analysis (Windham et al. 1988) and SmartMorph (www.meesoft.com) software. Warping, a nonlinear transformation, was done at the end of the registration to preserve image quality and information content.

Data Sampling and Feature Extraction:

TOMROP signals before and 25 minutes after CA injection (i.e., one pre-contrast set and the last post-contrast set) were used to extract the feature vectors for training the ANN. To generate a set that was physically meaningful, independent from system gain, and sensitive to the amount of the Gd-BSA concentration, inputs to the ANN were formed using the following:

$$U_n = \frac{S_{post}^n - S_{pre}^n}{S_{pre}^0} \quad (1)$$

$$n \in [1, 24]$$

where $S^n_{pre}$ is the TOMROP signal amplitude at echo n prior to contrast agent injection (pre Gd-BSA), $S^n_{post}$ is the TOMROP signal amplitude at echo n 25 minutes after contrast media injection, and $S^0_{pre}$ is the TOMROP signal amplitude at the $0^{th}$ echo. FIG. 3 illustrates $\{U_n\}$ versus post-inversion echoes for tumor and normal tissue areas respectively and demonstrates that, for the purpose of training the ANN, the two feature sets are well separated. An examination of FIG. 3 reveals that the later echoes (n≅10 to n=23) of the function $U_n$ for tumor and normal tissue areas are stably well separated, thus discriminating between areas of low and high CA concentration. While a systematic examination of the ideal number of echoes was not conducted, our experience was that when a shortened input vector (n<11 rather than n≤24) was attempted, the ANN trained poorly.

ANN Training:

A neural network with a feed forward multi-layer perceptron (MLP) architecture (Looney 1997) was used to estimate CA concentration. In this type of ANN, the nodes are organized in the input layer, hidden layers, and the output layer (FIG. 4A). The nodes are interconnected by weights in such a way that information propagates from one layer to the next through a sigmoid (bipolar) activation function; learning rate and momentum factors control the inter-node weight adjustment during the training. A back propagation learning strategy (Bagher-Ebadian et al. 2004; Freeman and Skapura 1991; Looney 1997; Rojas 1996) was employed for training the ANN in a supervised mode. In this strategy, a trial set of weights (the weight vectors, one vector for each layer of the ANN) is proposed. The input vectors (the set $\{U_n\}$—FIG. 4A) are input to the ANN, and the output result compared to the class identifier (in our case, to the autoradiogram). The weight vectors are then adjusted to maximize some measure of the agreement between the output of the ANN and the training set—in our case, this is defined by the Area Under the Receiver Operator Characteristic Curve ("AUROCC") (see below). In the training paradigm, since it provided the source-of-truth the autoradiogram was by definition taken to be error-free. See Appendix 1 below for further details of the back-propagation algorithm employed for training the multi-layer Perceptron ANN.

Batch processing was used to improve the convergence rate and the stability of training. The weight changes obtained from each training case were accumulated, and the weights updated after the entire set of training cases was evaluated. Batch processing improves stability, but with a tradeoff in the convergence rate (Looney 1997). A K-fold cross-validation ("KFCV") method was employed for training, testing, and network optimization (Bagher-Ebadian et al. 2004; Bishop 1997; Freeman and Skapura 1991; Gurney 1997; Looney 1997).

ANN Optimization and Calculation of the ANN Generalization Error:

To generalize our neural network, i.e., to allow its application to a wide range of inputs, we need to avoid both under-fitting of the training data (which generates a high variance in the output estimate) and over-fitting of the training data (which corresponds to high bias). There are a number of approaches for assuring generalization:

1. Optimize the number of free parameters (independent connection weights) in the model (e.g., the number of neurons in each layer and the number of layers).

2. Stop the gradient descent training at an appropriate point.

3. Add noise to the training patterns to smooth out the data points.

Number 3 is employed in cases where local minima 'trap' the ANN optimization process. Since no trapping was observed, strategy number 3 was not employed. To employ strategies number 1 and 2, we must estimate from our training data what the generalization error is likely be. To characterize the generalization error, we trained and validated the ANN by the KFCV method (Bishop 1997; Gurney 1997).

In K-Fold Cross-Validation the training data are divided at random into K distinct subsets, the network is then trained using K−1 subsets, and tested on the remaining subset. The process of training and testing is then repeated for each of the K possible choices of the subset omitted from the training. The average error, calculated by the area under the ROC curve of the ANN (see below) validated on the K omitted subsets then serves as the estimate of the generalization error. This procedure has the advantage that it allows us to use a high proportion of the available training data (a fraction (1−1/K) for training, while making use of all the data points in estimating the generalization error. The cost is that the process can be lengthy, since we need to train the network K times. Typically K~10 is considered reasonable. However, in this study to assure a very reliable estimate of the generalization error, K was set to 50 for 8100 samples (162 each fold) (Bishop 1997; Gurney 1997).

In some embodiments, the ANN constructed had a single output, an estimate of CA concentration. To measure how well this ANN matched the whole input dataset (each set $\{U_n\}$ for all TOMROP pixels) with the entire outcome set (each pixel in all autoradiograms), the ANN's Receiver Operator Characteristic ("ROC") was generated and the Area Under the ROC Curve ("AUROCC") (Basheer and Hajmeer 2000; Hanley and McNeil 1982) was calculated. The AUROCC gives a definitive measure of the estimator's discrimination ability that is not dependent upon the choice of decision threshold in the output of the ANN. The AUROCC provides a useful measure of discrimination levels i.e., how well the ANN can estimate the different levels of CA concentrations in a continuous range of the whole data set (Hanley and McNeil 1982). The Composite Simpson rule (Mathews and Fink 2004) for 2 m subintervals was employed to calculate the area under the ROC curve.

ROC curves were calculated as follows: at each epoch level during the KFCV procedure the output of the ANN was placed in the interval [0,1] with bins at intervals of 0.00126. The correct classification fraction ("CCF"), computed as the ratio of successful classification by the ANN to the total number of samples, given a specific threshold for success, was calculated for all different thresholds for the entire test set. The average CCFs for all split sets and each random trial were used to calculate the ROC curve. (Basheer and Hajmeer 2000; Hanley and McNeil 1982).

The AUROCC, or $A_z$-value, was used as an index to compare the ANN's performance, to determine the optimal architecture of the ANN, and to find the ANN termination error (Basheer and Hajmeer 2000; Hanley and McNeil 1982). Each KFCV set was trained until its error was below a defined termination error (i.e., the point at which the training procedure was stopped). The termination error was set by determining the error at the 90% point of the CCF's plateau.

The number of hidden layer nodes may affect the performance of the ANN classifier (Bagher-Ebadian et al. 2004; Freeman and Skapura 1991). Therefore, layer and node optimization were done by maximizing the AUROCC value for one hidden layer as a function of the number of nodes.

CA concentration maps estimated by the trained ANN ranged in value between 0 to 1.0. Finally, in order to present an easily understood comparison, the response of the trained ANN was compared to the QAR maps (gold standard) by calculating a correlation coefficient using all of the pixel comparisons available.

RESULTS

Twelve QAR maps, taken in 9 animals (one animal had 2, and another 3, analyzable slices respectively), were used to train and test the ANN. A set of 24 feature vectors (the set $\{U_n\}$) extracted from animal brains using Equation 1 were shown to the ANN and the performance of the ANN with respect to its number of hidden layer nodes was examined by considering the $A_z$-value at a KFCV termination error of 0.000158. The ANN was trained and tested for a set of 8100 samples using Equation 1.

A plot of the ROC curve and AUROCC ($A_z$—Test) versus number of neurons in the hidden layer is shown in FIGS. 4B and 4C for a stopping error of 0.000158. The maximum value of the AUROCC (0.86) gives the optimal number of neurons (6 neurons+1 bias) in the hidden layer. FIG. 4D plots the TSSE of the optimal ANN (25:7:1) versus epochs. Note the fast drop in the TSSE in FIG. 4D, plotted for an optimal ANN (25:7:1) with a learning rate of 0.01 and momentum of 0 for 8100 samples.

The trained ANN generated Gd-BSA concentration maps in the range 0 to 1.00. FIG. 5 shows selected outputs of the trained ANN in four animals, along with the corresponding autoradiogram. The left-hand image in all rows illustrates the QAR gold standard maps taken 30 minutes past injection of RISA, while the right-hand image in all rows presents the masked ANN response in the same animal and corresponding slice, from TOMROP inputs 25 minutes after CA injection. There is a clear visual correspondence between the ANN measures of CA concentration (bright areas in the right-hand images) and autoradiographic measures of RISA concentration (dark areas in the left-hand images).

To provide a more familiar evaluation of the value of the ANN as an estimator of CA concentration, ANN maps at 25 minutes after injection were compared to the corresponding autoradiogram for correlation. For a statistically reliable comparison, map sampling was done at a prevalence of about 0.5 by choosing two similar regions of interest ("ROI's") from normal tissue and leaky area. The ANN measure of CA concentration and QAR measure of RISA concentration are well correlated ($r=0.82$, $p<0.0001$).

Thus, in some of our work, a feature set extracted from TOMROP MRI images taken prior to the injection of Gd-BSA contrast agent, and at 25 minutes post-injection, was inputted to an ANN. The ANN was then trained by autoradiograms from the same animal, taken 30 minutes after the administration of $^{125}$I-RISA, in slices selected to correspond to the MRI images. Once trained, the ANN produced time-varying images of tissue concentration of CA that were highly correlated with the gold-standard autoradiograms. One great advantage of the trained ANN was that a complete estimate of the CA tissue concentration in an image set was available in seconds.

Our work addresses a fundamental problem in the matter of physiological estimates via time-concentration studies using MRI. The theory and practice of point estimation of the parameters of vascular physiology using the uptake and clearance of MRI CAs is well established (Ewing et al. 2006; Ostergaard et al. 1996a; Ostergaard et al. 1996b; Tofts et al. 1999). However, the major remaining problem is that of a reliable estimate of CA concentration versus time using MRI imaging techniques. This problem arises because the relaxation rates, $R_1$, $R_2$, and $R_2^*$, while linear in CA concentration in gels, are not linear in CA concentration in tissue, where the compartmentalization of water and/or CA becomes an important consideration. Thus, an ability to directly estimate CA concentration from MRI image sets provides a significant advantage in noninvasively evaluating cerebral physiology.

ANNs, while adept at point estimates in nonlinear systems, may not produce a reliable one-to-one result unless they are presented with a well-designed set of feature vectors. In our case, a knowledge of the physical nature of the TOMROP i.e., of a Look-Locker (Look and Locker 1970) signal response after magnetic inversion (Gelman et al. 2001) guided our choice of the feature vector set to be presented to the ANN (Equation 1). If it is assumed that $R_1$ and $R_2^*$ are approximately unimodal increasing as a function of contrast agent concentration, then equations 1 through 4b of Gelman et al. 2001 suggest that a gain-invariant feature vector defined by the set $\{U_n\}$ and combinations of its elements (the nature of these combinations to be defined by the ANN) might define a one-to-one relationship between a feature vector and a CA concentration. This is supported by our results presented herein.

In addition to these results, additional embodiments may comprise refinements that might be introduced to the practice of training an adaptive technology for the analysis of TOMROP image sets. First, the autoradiogram chosen for training was one 20 µm slice that corresponded to the center of the 2 mm thick MRI slice. As in previous practices of this sort (Ewing et al. 2003), an image formed by summing autoradiogram slices across a 2 mm section corresponding to the MRI slice may provide additional information beyond only the central slice.

Another refinement lies in the testing of other adaptive technologies. For instance, support vector regression ("SVR") (Drucker et al. 1996), a subset of support vector machines ("SVM's") (Burges 1998; Vapnik 1999) may be suitable. Also of interest are local linear neuro-fuzzy Models ("LLNFM's") (Jang 1993); these are neuro-fuzzy systems that provide robust learning capabilities and are adaptive networks themselves. LLNFM's are widely utilized in various applications such as pattern recognition, system identification, image processing and prediction. The local linear model tree is a type of Takagi-Sugeno-Kang (Takagi and Sugeno 1985) neuro-fuzzy algorithm which has proven its efficiency compared with other neuro fuzzy networks in learning nonlinear systems and pattern recognition. Optimal adaptive technique for application of embodiments to the problem of direct estimation of CA concentration is amenable to continuing investigation by those of ordinary skill in accordance with the teachings herein. These additional embodiments may extend at least to the estimation of CA concentration using such other, faster, sequences as dual-echo gradient-echo and echo-planar imaging ("EPI"). The utility of this extension is evident, since a major impediment to the estimation of vascular parameters is the nonlinear nature of image contrast to CA concentration. Thus, the availability of other adaptive technologies, each with its own strengths, may add to embodiments of the invention in providing a more direct estimate of CA concentration from MRI data.

The best feature vector set for presentation will vary with the sequence employed. In TOMROP (Look-Locker) types of sequence, both $T_1$ and $T_2^*$ affect signal amplitude and inversion recovery. The feature vector set $\{U_n\}$ was designed with this in mind, allowing the comparison of echo-to-echo differential, and pre- to post-injection amplitude, thus presenting the ANN with a feature set that was at least potentially independent in features that reflected the underlying MRI physics. In other sequences—e.g. fast gradient-echo, gradient-echo EPI, or spin-echo EPI, different mechanisms (i.e., $T_2$ rather than $T_2^*$ for spin-echo EPI) and/or different weights will apply to the various competing contrast mechanisms, possibly calling for different feature vector sets, and special instances of the basic MRI sequences—for instance, dual-echo gradient-echo sequences. Thus, feature vector sets and MRI sequences must be designed with the aim of presenting data that can be mapped one-to-one to CA concentration. It is important to remember that, with two contrast mechanisms, at least two distinct types of information must be presented to the ANN in order for the mapping to be one-to-one.

Some embodiments of the ANN might be dependent on the type of brain tissues and characteristics of pathological tissue. As one example only, the input vector found to be useful presented information about the rate of change of the Look-Locker signal to the ANN: more CA meant a faster rate of change, and thus presented a discriminant function to the neural network (Bagher-Ebadian et al. 2007). Since another major predictor of signal response to CA concentration is the intracellular ("ic") compartment volume relative to the extracellular ("ec") volume, we evaluated whether a measure well-known to reflect tissue water, i.e. $T_2$, would improve an ANN's ability to predict CA concentration. Accordingly, when a $T_2$-related map was added to the input vector set, the ANN's ability to estimate CA concentration in blood and normal tissue improved, demonstrating that inputs that characterize the tissue improve the predictive ability of the ANN.

With all elements—ROIs, training set, etc., remaining the same, the input vector set previously was expanded by the addition of a normalized map of $T_2^2$ (the $T_2$ map was squared because we discovered that the ANN trained better when the variation in $T_2$ was emphasized). $T_2$ was chosen because of the critical role that the ratio of ic to ec volumes plays in the ic-to-ec exchange rate of water protons. FIG. 6 shows an ANN predictor of contrast agent concentration, using as inputs the set $[\{Un\}, T_2^2]$. The sagittal sinus, tumor ROI, and normal tissue concentrations are plotted as a function of time across the duration of the experiment. The ratio of blood to normal tissue concentration is about 27:1, which is very close to the expected ratio for plasma concentrations in large vessels versus microvessels.

We also formed a set of 25 feature vectors (the set $\{Un\}+T_2^2$) was formed, where $\{U_n\}$ is the original feature set as follows:

$$U_n = \frac{S_{post}^n - S_{pre}^n}{S_{pre}^0}, \quad [9]$$
$$n \in [1, 24]$$

where $s_{pre}^n$ is the TOMROP signal amplitude at echo n prior to contrast agent injection (pre Gd-BSA), $s_{post}^n$ is the TOMROP signal amplitude at echo n 25 minutes after contrast media injection, and $s_{pre}^0$ is the TOMROP signal amplitude at the $0^{th}$ echo. This feature set was extracted from animal brains and shown to the ANN and the performance of the ANN with respect to its number of hidden layer nodes was examined by considering the $A_z$ value at a KFCV termination error of 0.000123. We found the optimum number of neurons in the hidden layer (five+1 bias) by maximization of the $A_z$-test at stopping error of 0.000123. The maximum value of the AUROCC (0.82) gives the optimal number of neurons (five neurons plus one bias) in the hidden layer. The ANN was trained and optimized ANN (25:6:1) with a learning rate of 0.01 and momentum of 0 for 8100 samples. The trained ANN's ability to predict CA concentration in various tissues appeared to improve in this embodiment. As an example, in the new maps of concentration (FIG. 6), the ratio of blood to normal tissue concentration is about 27:1. In major vessels, plasma volume is about 55% of blood volume, while in the microvascular bed (Bereczki et al. 1993a; Bereczki D et al. 1993b), it is about 73%. If CBV is 3%, then, one would expect the ratio of sagittal sinus plasma volume to tissue plasma volume (or CA concentration) to be about is 25:1. Thus, the ANN's prediction is very close to the expected ratio for plasma concentrations in large vessels versus microvessels.

In our work, the addition of $T_2$-related data demonstrates that the basis set of an ANN can be expanded, with an accompanying expansion of the network's ability to adjust its predictions to changing situations. It also demonstrates the ability of a well-trained ANN with an appropriate data set to extrapolate its predictions. As in previous training, the blood of the sagittal sinus was not included in the training set; nevertheless, the newly-trained ANN appears to be correctly estimating the concentration of CA in the sagittal sinus.

While the inclusion of the $T_2$-related map shows the utility of expanding the training set, it does not exhaust the possibilities for the inclusion of supplemental information, with inputs such as a normalized diffusion-weighted, and/or $T_1$-weighted images and/or unwrapped phase maps to allow the various tissue types (normal, tumor, infarct, blood) to be identified by the network. This strategy has proved reliable in tissue identification (Lu et al. 2005; Li, Jiang et al. 2005; Mitsias et al. 2004; Ding et al. 2004; Soltanian-Zadeh et al. 2003; Mitsias et al. 2002; Jacobs et al. 2000; Soltanian-Zadeh et al. 1998; Soltanian-Zadeh et al. 1997a; Soltanian-Zadeh et al. 1997b), and there is a very good chance that it will allow the ANN to estimate CA concentrations in all cerebral tissues.

We have also trained an ANN using maps of $\Delta R_1$. Inputs were the input vector set of equation 9, plus a map of $T_2^2$, as above. Rather than autoradiography, the training set consisted of maps of $\Delta R_1$ constructed from the Look-Locker data. FIG. 7 show related results: at the left, the output of an ANN trained using the input feature vectors of Eq 9, plus $T_2^2$, with ARGs as the training set, and at the right, the output of an ANN trained with the input feature vectors of Eq 9, plus $T_2^2$, but using $\Delta R_1$ as the training set.

Our work demonstrates that a map of $\Delta R_1$ obtained from a LL data set can be substituted for autoradiography as a training set in the development of an ANN.

In other prophetic embodiments, without limitation, an ANN may be constructed for each MRI pulse sequence. For variations in the pulse parameters, adding inputs to the ANN that account for critical variables may allow the ANN to better predict CA tissue concentration. For instance, in the dual-echo gradient-echo sequence (2GE sequence), data may be gathered across a range of tip-angles and repetition times, with the tip-angles and repetition times as additional inputs to the ANN. This, along with inputs to characterize tissue type, may allow the application of one ANN to a broad range of experimental conditions. Gathering data across a range of field strengths, and then inputting the field strengths to the ANN as additional inputs, may allow the trained ANN to estimate CA concentration in clinical studies.

APPENDIX I

Back propagation puts the difference between the class identifier and the ANN output back through the ANN to produce a set of error vectors that can be used as a summary measure. Using a set of training vectors and class identifiers to produce a sampling of errors under different conditions, the weights are then adjusted iteratively to reduce the total error measure to a minimum.

The units of the neural network (the neurons) are connected to one another. Connections correspond to the edges of the underlying directed graph. There is a real number associated with each connection, which is called the weight of the connection. We denote by $W_{ij}$ the weight of the connection from unit $u_i$ to unit $u_j$. It is then convenient to summarize the pattern of network connectivity by a weight matrix W whose elements are the weights $W_{ij}$. A positive weight represents an excitatory connection, and a negative weight an inhibitory connection.

A unit in the output layer determines its activity by following a two-step procedure:

First, it computes the total weighted input $x_j$, using the formula:

$$X_j = \sum_i y_i W_{ij} \quad (1)$$

where $y_i$ is the activity level of the $j^{th}$ unit in the previous layer and $W_{ij}$ is the weight of the connection between the $i^{th}$ and the $j^{th}$ unit. Next, the unit calculates the activity $y_j$ using some function of the total weighted input, which in this case is a sigmoid function. Once the activities of all output units are determined, the network computes the error E defined by the expression:

$$E = \frac{1}{2} \sum_i (y_i - d_i)^2, \quad (2)$$

where $y_j$ is the activity level of the $j^{th}$ unit in the top layer and $d_j$ is the desired output of the $j^{th}$ unit.

The back-propagation algorithm consists of four steps:

1. Compute the rate of change in the error as the activity of an output unit is changed. This error derivative ("EA") is the difference between the actual and the desired activity.

$$EA_j = \frac{\partial E}{\partial y_j} = y_i - d_i \quad (3)$$

2. Compute the rate of change in the error as the total input received by an output unit is changed. This quantity ("EI") is the answer from step 1 multiplied by the output rate of a unit as its total input is changed.

$$EI_j = \frac{\partial E}{\partial x_j} = \frac{\partial E}{\partial y_j} \times \frac{\partial y_j}{\partial x_j} = EA_j y_j (1 - y_j) \quad (4)$$

3. Compute the rate of change in the error as a weight on the connection into an output unit is changed. This quantity ("EW") is the answer from step 2 multiplied by the activity level of the unit from which the connection emanates.

$$EW_{ij} = \frac{\partial E}{\partial W_{ij}} = \frac{\partial E}{\partial x_j} \times \frac{\partial x_j}{\partial W_{ij}} = EI_j y_j \quad (5)$$

4. Compute the rate change of the error as the activity of a unit in the previous layer is changed. This crucial step allows back propagation to be applied to multilayer networks $EI_j y_j$. When the activity of a unit in the previous layer changes, it affects the activities of all the output units to which it is connected. Thus, to compute the overall effect on the error, all these separate effects are summed on the output units. Each effect is simple to calculate as the answer in step 2 multiplied by the weight on the connection to that output unit.

$$EA_i = \frac{\partial E}{\partial y_i} = \sum_j \frac{\partial E}{\partial x_j} \times \frac{\partial x_j}{\partial y_i} = \sum_j EI_j W_{ij} \quad (6)$$

Through steps 2 to 4, the EA's of one layer of units are converted into EA's for the previous layer. This procedure is repeated to get the EA's for as many previous layers as desired. Once the EA of a unit is known, steps 2 and 3 can be used to compute the EW's of its incoming connections.

All references are incorporated in full by reference as though fully set forth herein.

While the present invention has been particularly shown and described with reference to the foregoing alternative embodiments, it should be understood by those skilled in the art that various alternatives to the embodiments of the invention described herein may be employed in practicing the invention without departing from the spirit and scope of the invention as defined in the following claims. It is intended that the following claims define the scope of the invention and that the method and apparatus within the scope of these claims and their equivalents be covered thereby. This description of the invention should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element of the equivalent thereof, such claims should be understood to include incorporation of one or more such elements, neither requiring nor excluding two or more such elements.

TABLE OF REFERENCES

Bagher-Ebadian H, Soltanian-Zadeh H, Seayeshi S, Smith S T. (2004). Neural Network and Fuzzy Clustering Approach for Automatic Diagnosis of Coronary Artery Disease in Nuclear Medicine. *IEEE Transactions on Nuclear Science* 51:184-192.

Bagher-Ebadian H, Nagaraja T N, Paudyal R, Whitton P A, Panda S, Fenstermacher J D, Ewing J R. (2007). MRI Estimation of Contrast Agent Concentration in Tissue Using an Artificial Neural Network. *Magnetic Resonance in Medicine* 2007; 58(2):290-297.

Basheer I, Hajmeer M. (2000). Artificial neural networks: fundamentals, computing, design and application. *J Microbiol Meth* 43:3-31.

Bereczki D, Wei L, Otsuka T, Acuff V, Pettigrew K, Patlak C, Fenstermacher J. (1993a). Hypoxia Increases Velocity of Blood Flow Through Parenchymal Microvascular Systems in Rat Brain. *Journal of Cerebral Blood Flow and Metabolism* 1993; 13:475-486.

Bereczki D, Wei L, Otsuka T, Hans F-J, Acuff V, Patlak C, Fenstermacher J. (1993b). Hypercapnia slightly raises blood volume and sizably elevates flow velocity in brain microvessels. *American Journal of Physiology* 1993; 264: H1360-H1369.

Bishop C M. (1997). *Neural Networks for Pattern Recognition*. Oxford, United Kingdom: Oxford University Press.

Blasberg R G, Fenstermacher J D, Patlak C S. (1983). Transport of alpha-aminoisobutyric acid across brain capillary and cellular membranes. *J Cereb Blood Flow Metab* 3:8.

Boxerman J L, Schmainda K M, Weisskoff R M. (2006). Relative cerebral blood volume maps corrected for contrast agent extravasation significantly correlate with glioma tumor grade, whereas uncorrected maps do not. *AJNR Am J Neuroradiol* 27:859-867.

Brix G, Schad L R, Deimling M, Lorenz W J. (1990). Fast and Precise $T_1$ Imaging Using a TOMROP Sequence. *Magnetic Resonance Imaging* 8:351-356.

Burges C J C. (1998). A Tutorial on Support Vector Machines for Pattern Recognition. *Data Mining and Knowledge Discovery* 2:121-167.

Daldrup-Link H E, Okuhata Y, Wolfe A, Srivastav S, Oie S, Ferrara N, Cohen R L, Shames D M, Brasch R C. (2004). Decrease in tumor apparent permeability-surface area product to a MRI macromolecular contrast medium following angiogenesis inhibition with correlations to cytotoxic drug accumulation. *Microcirculation* 11:387-396.

Ding G, Jiang Q, Zhang L, Zhang Z, Knight R A, Soltanian-Zadeh H, Lu M, Ewing J R, Li Q, Whitton P A, Chopp M. (2004). Multiparametric ISODATA analysis of embolic stroke and rt-PA intervention in rat. *Journal of the Neurological Sciences* 2004; 223:135-143.

Drucker H, Burges C J C, Kaufman L, Smola A, Vapnik V. (1996). Support Vector Regression Machines. *Advances in Neural Information Processing Systems* 9:155-161.

Duda R O, Hart P E, Stork D G. (2001). *Pattern classification*. New York: Wiley & Sons.

Ewing J R, Knight R A, Nagaraja T N, Yee J S, Nagesh V, Whitton P A, Li L, Fenstermacher J D. (2003). Patlak plots of Gd-DTPA MRI data yield blood-brain transfer constants concordant with those of 14C-sucrose in areas of blood-brain opening. *Magnetic Resonance in Medicine* 50:283-292.

Ewing J R, Brown S L, Lu M, Panda S, Ding G, Knight R A, Cao Y, Jiang Q, Nagaraja T N, Churchman J L, Fenstermacher J D. (2006). Model selection in magnetic resonance imaging measurements of vascular permeability: Gadomer in a 9 L model of rat cerebral tumor. *J Cereb Blood Flow Metab* 26:310-320.

Freeman J, Skapura D. (1991). *Neural Network-Algorithms, Applications and Programming Techniques*. Reading, M A: Addison-Wesley.

Galbraith S M, Maxwell R J, Lodge M A, Tozer G M, Wilson J, Taylor N J, Stirling J J, Sena L, Padhani A R, Rustin G J. (2003). Combretastatin A4 phosphate has tumor antivascular activity in rat and man as demonstrated by dynamic magnetic resonance imaging. *J Clin Oncol* 21:2831-2842.

Gelman N, Ewing J R, Gorell J M, Spickler E M, Solomon E G. (2001). Interregional variation of longitudinal relaxation rates in human brain at 3.0 T: relation to estimated iron and water contents. *Magnetic Resonance in Medicine* 45:71-79.

Gurney K. (1997). *An Introduction to Neural Networks*. Abingdon, United Kingdom: Taylor & Francis Press.

Hanley J, McNeil B. (1982). The meaning and use of the area under the Receiver Operating Characteristic (ROC) curve. *Radiology* 143:29-36.

Haykin S. (1999). *Neural Networks: A Comprehensive Foundation*. New York: Prentice Hall.

Jacobs M A, Knight R A, Soltanian-Zadeh H, Zheng Z G, Goussev A V, Peck D J, Windham J P, Chopp M. (2000). Unsupervised Segmentation of Multiparameter MRI in Experimental Cerebral Ischemia with Comparison to T2, Diffusion, and MRI Parameters and Histopathological Validation. *Journal of Magnetic Resonance Imaging* 2000; 11:425-437.

Jang J R. (1993). ANFIS: Adaptive network based fuzzy inference system. *IEEE Transactions: Systems, Man and Cybernetics* 23:665-685.

Johnson G, Wetzel S G, Cha S, Babb J, Tofts P S. (2004). Measuring blood volume and vascular transfer constant from dynamic, T(2)*-weighted contrast-enhanced MRI. *Magnetic Resonance in Medicine* 51:961-968.

Landis C S, Li X, Telang F W, Coderre J A, Micca P L, Rooney W D, Latour L L, Vetek G, Palyka I, Springer C S, Jr. (2000). Determination of the MRI contrast agent concentration time course in vivo following bolus injection: effect of equilibrium transcytolemmal water exchange. *Magn Reson Med* 44:563-574.

Li, Jiang Q, Ding G, Zhang L, Zhang Z G, Ewing J R, Knight R A, Kapke A, Soltanian-Zadeh H, Chopp M. (2005). Map-ISODATA demarcates regional response to combination rt-PA and 7E3 F(ab')(2) treatment of embolic stroke in the rat. *J Magn Reson Imaging* 2005; 21(6):726-734.

Li X, Rooney W D, Springer C S, Jr. (2005). A unified magnetic resonance imaging pharmacokinetic theory: intravascular and extracellular contrast reagents. *Magnetic Resonance in Medicine* 54:1351-1359.

Look D C, Locker D R. (1970). Time Saving in Measurement of NMR and EPR Relaxation Times. *Review of Scientific Instruments* 41:250-251.

Looney C G. (1997). *Pattern recognition using neural networks: theory and algorithms for engineers and scientists*. New York: Oxford University Press.

Lu M, Mitsias P D, Ewing J R, Soltanian-Zadeh H, Bagher-Ebadian H, Zhao Q, Oja-Tebbe N, Patel S C, Chopp M. (2005). Predicting final infarct size using acute and subacute multiparametric MRI measurements in patients with ischemic stroke. *J Magn Reson Imaging* 2005; 21(5):495-502.

Mathews J H, Fink K K. (2004). *Numerical Methods Using Matlab*. Upper Saddle River, N.J., USA: Prentice-Hall Inc.

McCulloch W, Pitts W. (1943). A Logical Calculus of the Ideas Immanent in Nervous Activity. *Bulletin of Mathematical Biophysics* 5:115-133.

Mitsias P D, Jacobs M A, Hammoud R, Pasnoor M, Santhakumar S, Papamitsakis N I, Soltanian-Zadeh H, Lu M, Chopp M, Patel S C. (2002). Multiparametric MRI ISODATA ischemic lesion analysis: correlation with the clinical neurological deficit and single-parameter MRI techniques. *Stroke* 2002; 33(12):2839-2844.

Mitsias P D, Ewing J R, Lu M, Khaligi M M, Pasnoor M, Ebadian H B, Zhao Q, Santhakumar S, Jacobs M A, Papamitsakis N, Soltanian-Zadeh H, Hearshen D, Patel S C, Chopp M. (2004). Multiparametric iterative self-organizing MR imaging data analysis technique for assessment of tissue viability in acute cerebral ischemia. *AJNR Am J Neuroradiol* 2004; 25(9):1499-1508.

Nagaraja T N, Croxen R L, Panda S, Knight R A, Keenan K A, Brown S L, Fenstermacher J D, Ewing J R. (2006). Application of arsenazo III in the preparation and characterization of an albumin-linked, gadolinium-based macromolecular magnetic resonance contrast agent. *J Neurosci Methods* 157:238-245.

Nakagawa H, Groothuis D R, Owens E S, Fenstermacher J D, Patlak C S, Blasberg R G. (1987). Dexamethasone effects on [125-I]albumin distribution in experimental RG-2 gliomas and adjacent brain. *Journal of Cerebral Blood Flow and Metabolism* 7:687-701.

Ostergaard L, Weisskoff R M, Chesler D A, Gyldensted C, Rosen B R. (1996a). High Resolution Measurement of Cerebral Blood Flow using Intravascular Tracer Bolus Passages. Part I: Mathematical Approach and Statistical Analysis. *Magnetic Resonance in Medicine* 36:715-725.

Ostergaard L, Weisskoff R M, Chesler D A, Gyldensted C, Rosen B R. (1996b). High Resolution Measurement of Cerebral Blood Flow using Intravascular Tracer Bolus Passages. *Part II: Experimental Comparison and Preliminary Results. Magnetic Resonance in Medicine* 36:726-736.

Rempp K A, Brix G, Wenz F, Becker C R, Guckel F, Lorenz W J. (1994). Quantification of Regional Cerebral Blood Flow and Volume with Dynamic Susceptibility Contrast-enhanced MR Imaging. *Radiology* 193:637-641.

Rojas R. (1996). *Neural Networks: A Systematic Introduction*. Berlin: Springer-Verlag Soltanian-Zadeh H, Windham J P, Robbins L. (1997a). Semi-Supervised Segmentation Supervised Segmentation of MRI Stroke Studies. *International Society of Optical Eng (SPIE)*. Volume 3034. Newport Beach, Calif.: SPIE; 1997. p 437-448.

Soltanian-Zadeh H, Windham J P. (1997b). A Multi-resolution Approach for Intracranial Volume Segmentation from Brain Images. *Medical Physics* 1997; 24(12):1844-1853.

Soltanian-Zadeh H, Windham J P, Peck D J, Mikkelsen T. (1998). Feature Space Analysis of MRI. *Magnetic Resonance in Medicine* 1998; 40:443-453.

Soltanian-Zadeh H, Pasnoor M, Hammoud R, Jacobs M A, Patel S C, Mitsias P D, Knight R A, Zheng Z G, Lu M, Chopp M. (2003). MRI tissue characterization of experimental cerebral ischemia in rat. *J Magn Reson Imaging* 2003; 17(4):398-409.

Takagi T, Sugeno M. (1985). Fuzzy identification of systems and its applications to modeling and control," vol. 15, pp. 116-132, 1985. *IEEE Transactions: Systems, Man and Cybernetics* 15:116-132.

Tofts P S, Brix G, Buckley D L, Evelhoch J L, Henderson E, Knopp M V, Larsson H B, Lee T Y, Mayr N A, Parker G J, Port R E, Taylor J, Weisskoff R M. (1999). Estimating kinetic parameters from dynamic contrast-enhanced T(1)-weighted MRI of a diffusable tracer: standardized quantities and symbols. *J Magn Reson Imaging* 10:223-232.

Vapnik V. (1999). *The Nature of Statistical Learning Theory*. New York: Springer Verlag.

Williamson J. (1996). The Sievert integral revisited: evaluation and extension to 125I, 169Yb, and 192Ir brachytherapy sources. *International Journal of Radiation Oncology, Biology, Physics* 36:1239-1250.

Windham J P, Abd-Allah M A, Reimann D A, Froelich J W, Haggar A M. (1988). Eigenimage Filtering in MR Imaging. *Journal of Computer Assisted Tomography* 12:1-9

Wismuller A, Meyer-Baese A, Lange O, Reiser M F, Leinsinger G. (2006). Cluster analysis of dynamic cerebral contrast-enhanced perfusion MRI time-series. *IEEE Trans Med Imaging* 25:62-73.

Yankeelov T E, Rooney W D, Li X, Springer C S. (2003). Variation of the Relaxographic "Shutter-Speed" for Transcytoliemmal Water Exchange Affects the CR Bolus-Tracking Curve Shape. *Magnetic Resonance in Medicine* 50:1151-1169.

What is claimed is:

1. A method comprising:
   providing an adaptive neural network with training criterion image data of known radioactive contrast agent concentration in biological tissue,
   providing the adaptive neural network with MRI image data from a patient before injection of a radioactive MRI contrast agent into the patient,
   providing the adaptive neural network with MRI image data from the patient after injection of a radioactive MRI contrast agent into the patient, the adaptive neural network measuring any change between the MRI image data from a patient before injection of a radioactive MRI contrast agent into the patient and the MRI image data from the patient after injection of a radioactive MRI contrast agent into the patient,
   and
   comparing the training criterion data of known radioactive agent concentration with any change in MRI image data from the patient after injection of the radioactive contrast agent and measuring the concentration of radioactive contrast agent in the post-injection MRI image as a continuous variable, each by using the adaptive neural network;
   wherein the MRI image data from the patient before injection and the MRI image data from the patient after injection are each prepared from MRI tissue magnetization according to at least one of the following steps:
   a. inverting the magnetization of the tissue and measuring any recovery of the tissue magnetization with further MRI imaging, or
   b. perturbing the magnetization of the tissue with a known tip-angle, and measuring any decrease of tissue magnetization with further MRI imaging, or
   c. perturbing the magnetization of the tissue with a set of known tip-angles and measuring the changes in tissue magnetization with further MRI imaging;
   wherein the radioactive MRI contrast agent injected into the patient comprises a gadolinium labeled agent; and
   wherein the training criterion image data are derived from autoradiographic images of tissue radioactive contrast agent administration to a mammal.

2. The method of claim 1, wherein the radioactive MRI contrast agent comprises gadolinium labeled serum albumin.

3. The method of claim 2, wherein the radioactive contrast agent used to generate the training criterion image data of known radioactive contrast agent concentration comprises radioactive serum albumin.

4. A method comprising:
   providing an adaptive neural network with training criterion image data of known radioactive contrast agent concentration and matching data: (a) of tissue relaxation rate R1 before and after administration of MRI contrast agent in an experimental animal, or (b) of tissue relaxation rate R1 before and after administration of MRI contrast agent in a human,
   providing the adaptive neural network with MRI image data from a patient or experimental animal before injection of a radioactive MRI contrast agent into the patient or the experimental animal,
   providing the adaptive neural network with MRI image data from the patient or experimental animal after injection of a radioactive MRI contrast agent into the patient or the experimental animal, the adaptive neural network measuring any change between the MRI image data from a patient before injection of a radioactive MRI contrast agent into the patient and the MRI image data from the patient after injection of a radioactive MRI contrast agent into the patient or experiment animal,
   and
   comparing the training criterion data of known radioactive agent concentration with any change in MRI image data from the patient or experimental animal after injection of the radioactive MRI contrast agent and measuring the concentration of radioactive contrast agent in the post-injection MRI image as a continuous variable, each by using the adaptive neural network;
   wherein the MRI image data from the patient or experimental animal before injection and the MRI image data from the patient or experimental animal after injection are each prepared from MRI tissue magnetization according to at least one of the following steps:
a. inverting the magnetization of the tissue and measuring any recovery of the tissue magnetization with further MRI imaging, or
b. perturbing the magnetization of the tissue with a known tip-angle, and measuring any decrease of tissue magnetization with further MRI imaging, or
c. perturbing the magnetization of the tissue with a set of known tip-angles and measuring the changes in tissue magnetization with further MRI imaging;

wherein the radioactive MRI contrast agent injected into the patient or experimental comprises a gadolinium labeled agent; and wherein the training criterion image data are derived from autoradiographic images of tissue radioactive contrast agent administration to a mammal.

5. The method of claim 4, wherein the radioactive MRI contrast agent comprises gadolinium labeled serum albumin.

6. The method of claim 5, wherein the radioactive contrast agent used to generate the training criterion image data of known radioactive contrast agent concentration comprises radioactive serum albumin.

* * * * *